(12) United States Patent
Huang et al.

(10) Patent No.: US 8,871,360 B2
(45) Date of Patent: Oct. 28, 2014

(54) ORGANOMETALLIC COMPOUND AND ORGANIC ELECTROLUMINESCENCE DEVICE EMPLOYING THE SAME

(75) Inventors: Heh-Lung Huang, New Taipei (TW); Teng-Chih Chao, Pingjhen (TW); Hao-Chun Lee, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 279 days.

(21) Appl. No.: 13/360,217

(22) Filed: Jan. 27, 2012

(65) Prior Publication Data

US 2013/0033172 A1 Feb. 7, 2013

(30) Foreign Application Priority Data

Aug. 5, 2011 (TW) .............................. 100127917 A

(51) Int. Cl.
H01L 51/54 (2006.01)
C09K 11/06 (2006.01)
H01L 51/00 (2006.01)
C07F 15/00 (2006.01)
H01L 51/50 (2006.01)

(52) U.S. Cl.
CPC ............ C09K 11/06 (2013.01); H01L 51/0085 (2013.01); C07F 15/0033 (2013.01); C09K 2211/1051 (2013.01); C09K 2211/185 (2013.01); C09K 2211/1037 (2013.01); H01L 51/5016 (2013.01); Y10S 428/917 (2013.01)
USPC .... 428/690; 428/917; 313/504; 257/E51.044; 546/10

(58) Field of Classification Search
None
See application file for complete search history.

(56) References Cited

U.S. PATENT DOCUMENTS

| 3,192,197 | A | 6/1965 | Dietrich et al. |
| 7,445,857 | B2 | 11/2008 | Shen et al. |
| 2003/0068526 | A1 | 4/2003 | Kamatani et al. |
| 2006/0014047 | A1 | 1/2006 | Takiguchi et al. |
| 2006/0199836 | A1 | 9/2006 | Turtle et al. |
| 2007/0237981 | A1 | 10/2007 | Shen et al. |

FOREIGN PATENT DOCUMENTS

| EP | 0 812 826 A1 | 12/1997 |
| JP | 2003-109758 A | 4/2003 |
| JP | 2003-234192 | 8/2003 |
| JP | 2005-276799 | 10/2005 |
| JP | 2009-046435 A | 3/2009 |
| TW | I242999 B | 11/2005 |
| TW | 200623955 A | 7/2006 |
| WO | WO 2010033550 | 3/2010 |
| WO | WO 2010118029 | 10/2010 |

OTHER PUBLICATIONS

Chien et al., "Efficient red electrophosphorescence from a fluorene-based bipolar host material", Organic Electronics, vol. 10, (2009), pp. 871-876.
Duan et al., "New Iridium Complexes as Highly Efficient Orange-Red Emitters in Organic Light-Emitting Diodes", Advanced Materials, vol. 15, No. 3, Feb. 5, 2003, pp. 224-228.
Huang et al., "Uniform dispersion of triplet emitters in multi-layer solution-processed organic light-emitting diodes", Synthetic Metals, vol. 160, (2010), pp. 2393-2396.
Lee et al., "Cyclometalated iridium(III) complexes with 5-acetyl-2-phenypyridine derived ligands for red phosphorescent OLEDs", Synthetic Metals, vol. 161, (2011), pp. 1113-1121.
Lui et al., "Structural Characterization of Co•Bleomycin A2 Brown:Free and Bound to d(CCAGGCCTGG)", Journal of the American Chemical Society, vol. 119, 1997, pp. 9603-9613.
Shen et al., "Novel Synthesis of o-Naphthothiophenequinone Derivatives via Regioselective Diels—Alder Reaction", Tetrahedron, vol. 61, (2005), pp. 9097-9101.
Taiwan Office Action for Appl. No. 100127917 dated Jul. 23, 2013 (w/engl. translation).

*Primary Examiner* — Marie R. Yamnitzky
(74) *Attorney, Agent, or Firm* — Birch, Stewart, Kolasch & Birch, LLP

(57) ABSTRACT

Organometallic compounds and organic electroluminescence devices employing the same are provided. The organometallic compound has a chemical structure represented below:

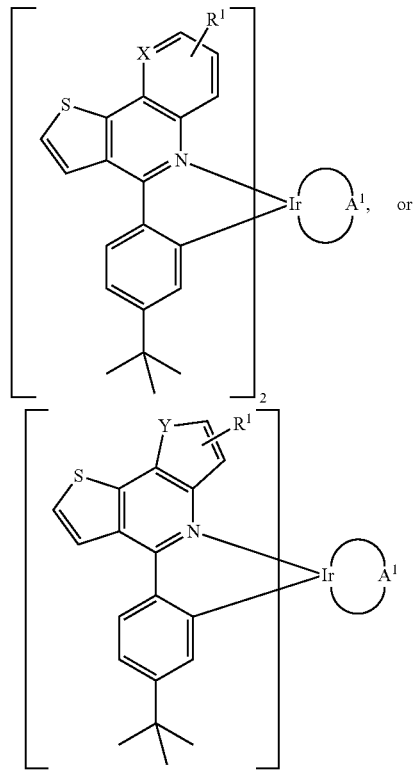

wherein, X is C—H or N, Y is $CH_2$ or NH; $R^1$ is H, or $C_{1-8}$ alkyl; and $A^1$ is acetylacetone ligand, acetylacetone with phenyl group ligand, or derivatives thereof.

5 Claims, 1 Drawing Sheet

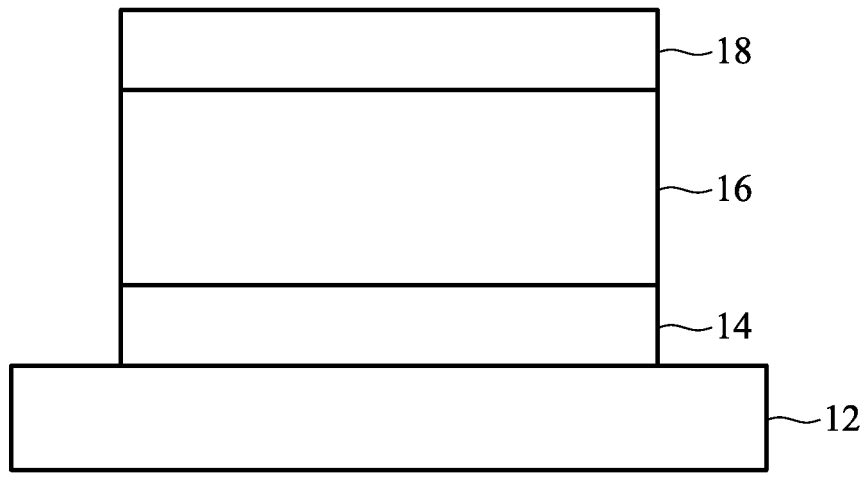

ORGANOMETALLIC COMPOUND AND ORGANIC ELECTROLUMINESCENCE DEVICE EMPLOYING THE SAME

CROSS REFERENCE TO RELATED APPLICATIONS

This application is based upon and claims the benefit of priority from the prior Taiwan Patent Application No. 100127917, filed on Aug. 5, 2011, the entire contents of which are incorporated herein by reference.

BACKGROUND

1. Field

The disclosure relates to an organometallic compound and organic electroluminescence device employing the same and, more particularly, to a phosphorescent organometallic compound and a phosphorescent organic electroluminescence device employing the same.

2. Description

Recently, with the development and wide application of electronic products, such as mobile phones, PDAs, and notebook computers, there has been increasing demand for flat display elements which consume less electric power and occupy less space. Organic electroluminescent devices are self-emitting and highly luminous, with wide viewing angles, fast response speeds, and simple fabrication methods, making them an industry display of choice.

Generally, an organic electroluminescent device is composed of a light-emission layer sandwiched between a pair of electrodes. When an electric field is applied to the electrodes, the cathode injects electrons into the light-emission layer and the anode injects holes into the light-emission layer. When the electrons recombine with the holes in the light-emission layer, excitons are formed. Recombination of the electron and hole results in light emission.

Depending on the spin states of the hole and electron, the exciton, which results from the recombination of the hole and electron, can have either a triplet or singlet spin state. Luminescence from a singlet exciton results in fluorescence whereas luminescence from a triplet exciton results in phosphorescence. The emissive efficiency of phosphorescence is three times that of fluorescence. Therefore, it is crucial to develop highly efficient phosphorescent material, in order to increase the emissive efficiency of an OLED.

Conventional red phosphorescent materials, however, exhibit lower electroluminescent efficiency, thereby it is difficult to fabricate a high CRI white electroluminescent device by employing conventional red phosphorescent materials. Further, a red light emitted by an OLED is useful for wound healing and thus it the can be utilized for the development of therapeutics for wounds.

Therefore, it is necessary to develop novel organic compounds suitable for red phosphorescent OLEDs to solve the above problems.

BRIEF SUMMARY

An exemplary embodiment of an organometallic compound has a Formula (I) or Formula (II), of:

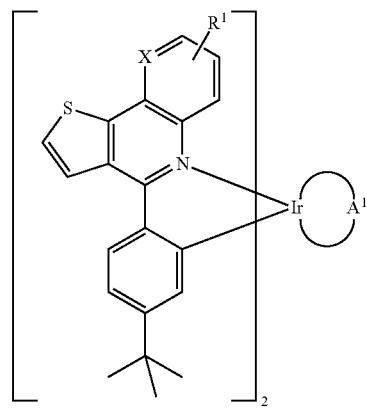

Formula (I)

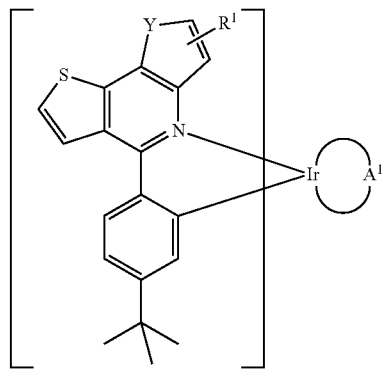

Formula (II)

wherein, X is C—H or N, Y is $CH_2$ or NH; $R^1$ is H, or $C_{1-8}$ alkyl; and $A^1$ is acetylacetone ligand, acetylacetone with phenyl group ligand, or derivatives thereof.

In another exemplary embodiment of the disclosure, an organic electroluminescent device is provided. The device includes a pair of electrodes and an electroluminescent element disposed between the pair of electrodes, wherein the electroluminescent element includes the aforementioned organometallic compound (serving as a red dopant).

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein:

FIG. 1 shows a cross section of an organic electroluminescent device disclosed by an embodiment of the disclosure.

DETAILED DESCRIPTION

The following description is of the best-contemplated mode of carrying out the disclosure. This description is made for the purpose of illustrating the general principles of the disclosure and should not be taken in a limiting sense. The scope of the disclosure is best determined by reference to the appended claims.

The disclosure provides an organometallic compound prepared by introducing a 4-phenylnaphtho[1,2-b]thiophene moiety, wherein an obtained organometallic compound is suitable for use in an electroluminescence device for emitting red light. Moreover, the organometallic compound of the disclosure can be applied in an organic electroluminescent device for enhancing the electroluminescent efficiency thereof.

Organometallic Compound

The disclosure provides an organometallic compound having a structure represented by Formula (I) or Formula (II):

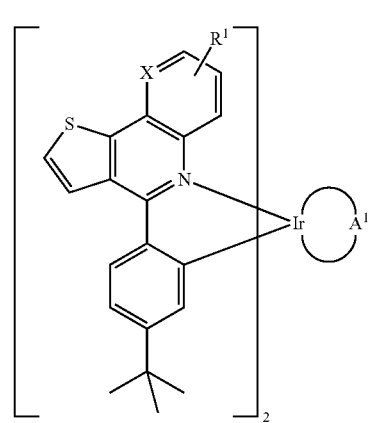

Formula (I)

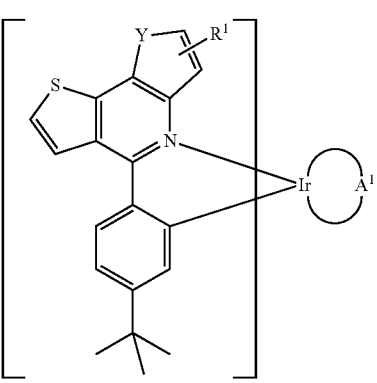

Formula (II)

wherein, X is C—H or N, Y is $CH_2$ or NH; $R^1$ is H, or $C_{1-8}$ alkyl; and $A^1$ is acetylacetone ligand, acetylacetone with phenyl group ligand, or derivatives thereof. Further, $R^1$ can be a methyl group, ethyl group, propyl group, isopropyl group, butyl group, tert-butyl group, pentyl group, or hexyl group.

According to an embodiment of the disclosure, $A^1$ is bonded with Ir via an oxygen atom on one side, and bonded with Ir via another oxygen atom on the other side.

According to some embodiments of the disclosure, the organometallic compound of the disclosure can have a structure represented by Formula (III), Formula (IV) or Formula (V), of:

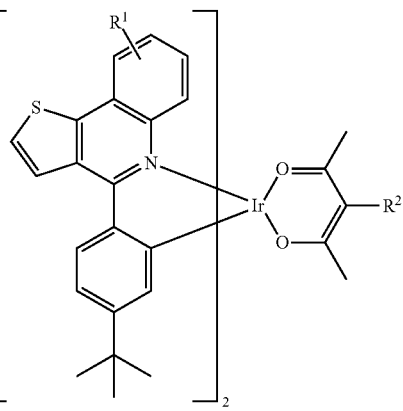

Formula (III)

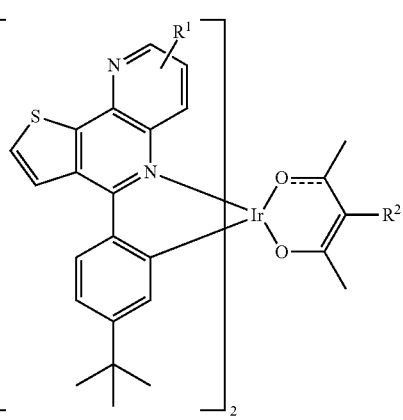

Formula (IV)

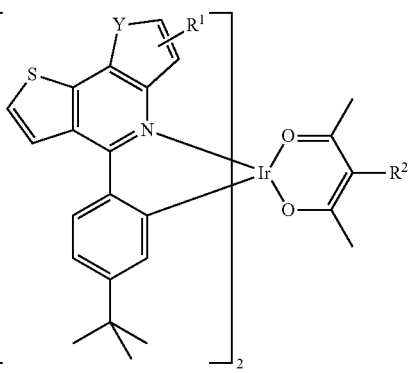

Formula (V)

wherein, $R^1$ is hydrogen, or $C_{1-8}$ alkyl group; $R^2$ is hydrogen, phenyl, or biphenyl; and Y is $CH_2$, or NH.

The organometallic compounds according to Formula (I) and Formula (II) of the disclosure include the following compounds shown in Table 1. In addition, the contraction thereof are also named and shown in Table 1.

TABLE 1

| Example | structure | contraction |
|---------|-----------|-------------|
| 1 | 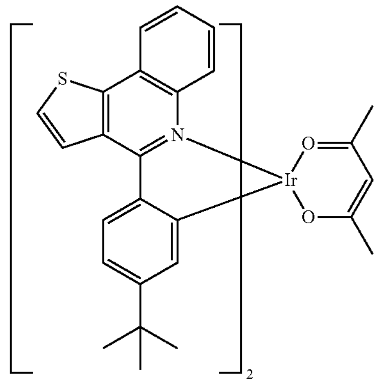 | Ir-THQ-acac |
| 2 | 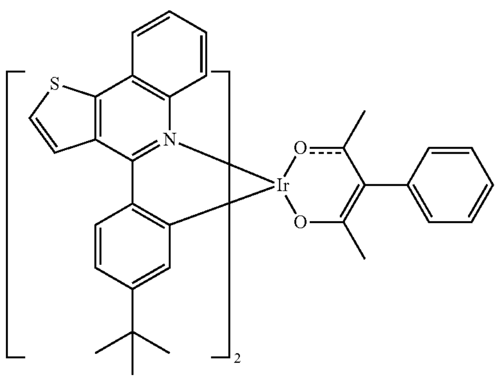 | Ir-THQ-phac |
| 3 | 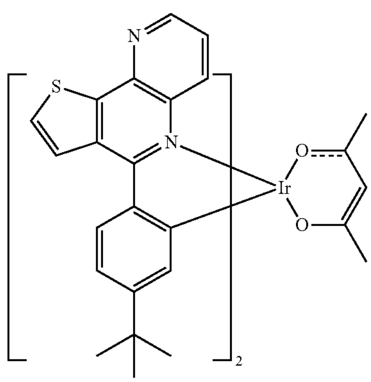 | Ir-THQ-N-acac |
| 4 | 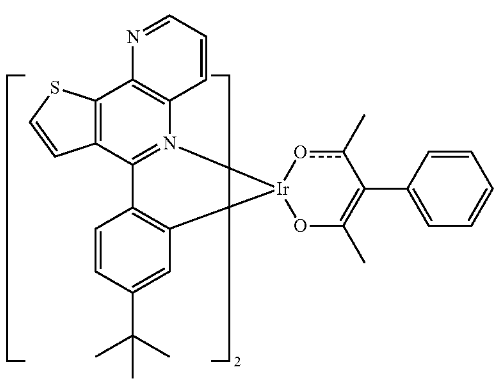 | Ir-THQ-N-phac |

In order to clearly illustrate the method for preparing organometallic compounds according to Formula (I) and Formula (II), the preparation of compounds disclosed in Examples 1-4 are described in detail as below.

Example 1

Preparation of Compound Ir-THQ-acac

First, compound (1) (2-(2-aminoethyl)thiophene, 2.0 g, 10.0 mmol) and 50 mL toluene were added into a 250 mL bottle. Next, compound (2) (1.29 g, 10.00 mmole), $K_2CO_3$ (2M, 20 mL), $Pd(PPH_3)_4$ (0.43 g), and $(t-Bu)_3P$ (0.23 g) were added into the bottle at room temperature. After heating to reflux, the NaOH aqueous solution (20%) was added into the bottle and stirred overnight. After purification, compound (3) with a yield of 69% was obtained. The synthesis pathway was as follows:

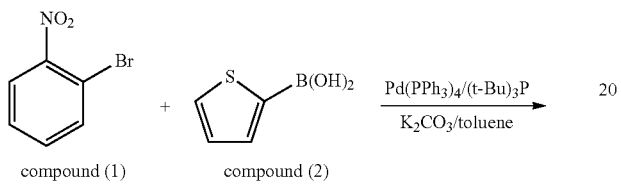

compound (1)    compound (2)

Next, compound (3) (1.0 g, 4.90 mmol), Iron powder, a mixed solvent ($EtOH:AcOH:H_2O=2:2:1$, 50 mL) were added into a 250 mL bottle. After heating to reflux for 15 min, the mixture was stirred at room temperature for 25 min. After filtration to remove the Iron powder, the result was neutralized by $NaHCO_3$ and then extracted by ethyl acetate and water. After concentration, compound (4) with a yield of 91% was obtained. The synthesis pathway was as follows:

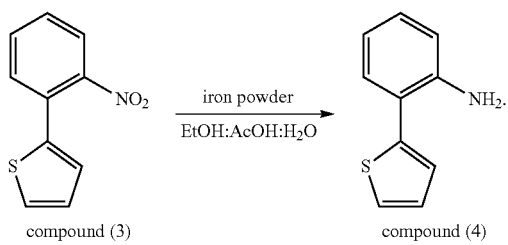 [SMILES: O=[N+]([O-])c1ccccc1-c1cccs1 ; Nc1ccccc1-c1cccs1]

compound (3)    compound (4)

Next, compound (4) (1.00 g, 5.70 mmole) and toluene (100 mL) were added into a 250 mL bottle. After heating to reflux, trifluoroacetic acid (1 eq) and compound (5) (0.97 g) were added into the bottle. Next, the mixture was heated to reflux under an oxygen atmosphere. After reaction, compound (6) with a yield of 79% was obtained. The synthesis pathway was as follows:

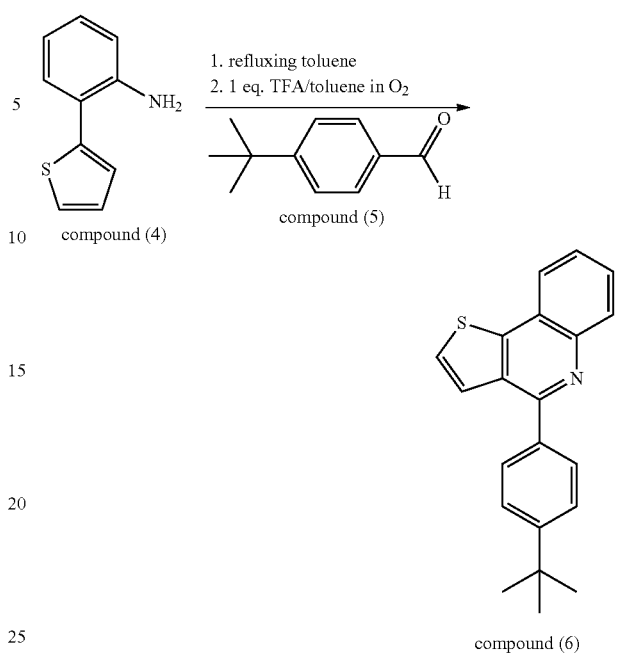

compound (4)    compound (5)

compound (6)

Next, compound (6) (3.68 g, 11.60 mmol), $IrCl_3 \cdot xH_2O$ (1.65 g), 2-methoxy ethanol (15 mL), and water (5 mL) were added into a 100 mL bottle. After heating to 140° C. for 24 hrs, acac

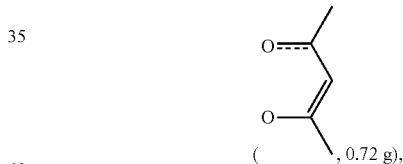

( , 0.72 g), $K_2CO_3$ (0.76 g), and 30 mL 2-methoxyethanol were added into the bottle. After reacting for 24 hrs, the bottle was cooled down to room temperature and the reaction was quenched by adding water (50 mL). The result was purified by column chromatography with n-hexane/dichloromethane (3:1), obtaining Ir-THQ-acac. The synthesis pathway was as follows:

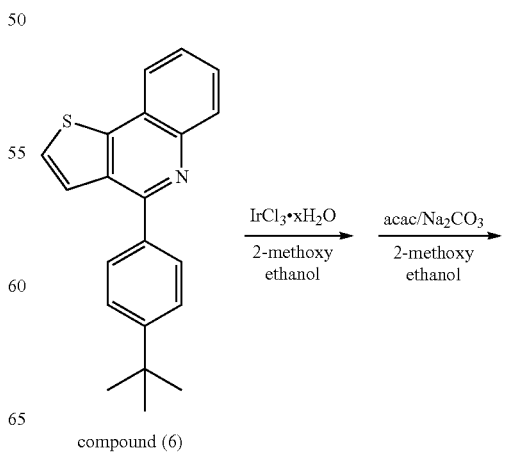

compound (6)

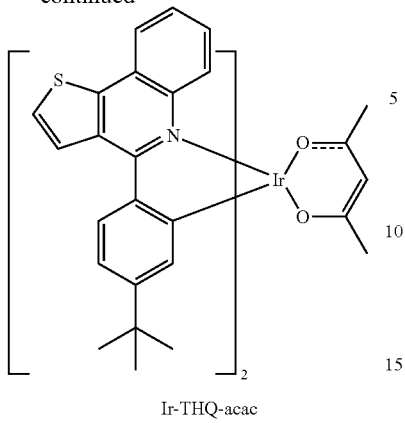

Ir-THQ-acac

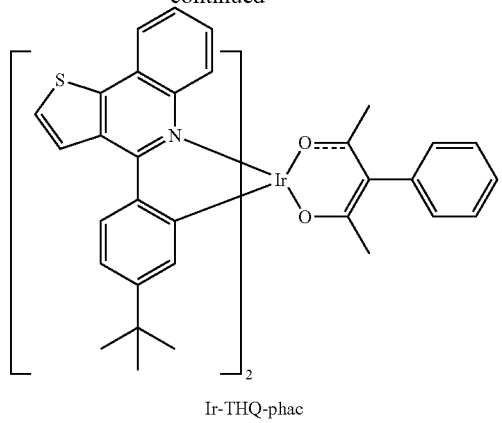

Ir-THQ-phac

The physical measurement of the compound Ir-THQ-acac is listed below:

$^1$H NMR (CDCl$_3$, 200 MHz) δ 8.49 (d, J=5.4 Hz, 2H), 8.41 (d, J=8.8 Hz, 2H), 8.23 (d, J=8.4 Hz, 2H), 8.02 (d, J=7.6 Hz, 2H), 7.69 (d, J=5.4 Hz, 2H), 7.44 (t, J=8.0 Hz, 2H), 7.28 (t, J=8.0 Hz, 2H), 7.03 (dd, J=8.0, 1.8 Hz, 2H), 6.71 (d, J=1.8 Hz, 2H), 4.47 (s, 1H), 1.35 (s, 6H), 0.88 (s, 18H).

Example 2

Preparation of Compound Ir-THQ-phac

First, compound (6) (3.68 g, 11.60 mmol), IrCl$_3$.xH$_2$O (1.65 g), 2-methoxy ethanol (15 mL), and water (5 mL) were added into a 100 mL bottle. After heating to 140° C. for 24 hrs, compound (7) (1.30 g), K$_2$CO$_3$ (0.76 g), and 30 mL 2-methoxyethanol were added into the bottle. After reacting for 24 hrs, the bottle was cooled down to room temperature and the reaction was quenched by adding water (50 mL). The result was purified by column chromatography with n-hexane/dichloromethane (3:1), obtaining Ir-THQ-phac. The synthesis pathway was as follows:

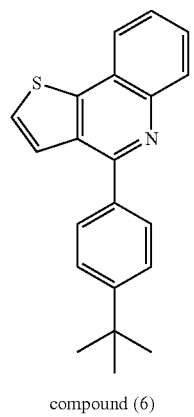

compound (6)

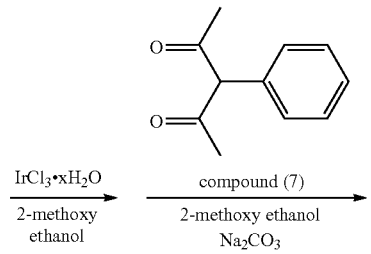

compound (7)

The physical measurement of the compound Ir-THQ-phac is listed below:

$^1$H NMR (CDCl$_3$, 200 MHz) δ 8.51 (d, J=5.4 Hz, 2H), 8.45 (d, J=8.8 Hz, 2H), 8.28 (d, J=8.4 Hz, 2H), 8.08 (d, J=7.6 Hz, 2H), 7.71 (d, J=5.4 Hz, 2H), 7.66 (d, J=8.0 Hz, 2H), 7.46 (t, J=8.0 Hz, 2H), 7.41 (d, J=1.8 Hz, 1H), 7.28 (t, J=8.0 Hz, 2H), 7.13 (dd, J=8.0, 1.8 Hz, 2H), 7.03 (dd, J=8.0, 1.8 Hz, 2H), 6.73 (d, J=1.8 Hz, 2H), 1.36 (s, 6H), 0.89 (s, 18H).

Example 3

Preparation of Compound Ir-THQ-N-acac

First, compound (1) (2-(2-aminoethyl)thiophene, 2.02 g, 10.0 mmol) and 50 mL toluene were added into a 250 mL bottle. Next, compound (9) (1.29 g, 10.00 mmole), K$_2$CO$_3$ (2M, 20 mL), Pd(PPH$_3$)$_4$ (0.43 g), and (t-Bu)$_3$P (0.23 g) were added into the bottle at room temperature. After heating to reflux, the NaOH aqueous solution (20%) was added into the bottle and stirred overnight. After purification, compound (10) was obtained. The synthesis pathway was as follows:

Next, compound (10) (1.0 g, 4.90 mmol), Iron powder (2.17 g, 38.90 mmol), a mixed solvent (EtOH:AcOH:H$_2$O=2:2:1, 50 mL) were added into a 250 mL bottle. After heating to reflux for 15 min, the mixture was stirred at room temperature for 25 min. After filtration to remove the Iron powder, the result was neutralized by NaHCO$_3$ and then extracted by ethyl acetate and water. After concentration, compound (11) was obtained. The synthesis pathway was as follows:

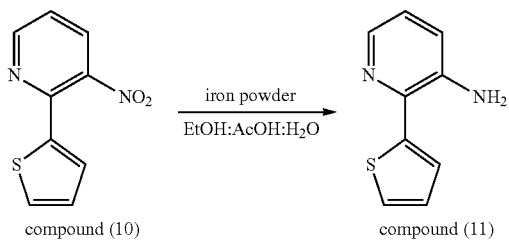 [SMILES: O=[N+]([O-])c1cccnc1-c1cccs1 ; Nc1cccnc1-c1cccs1]

compound (10) → compound (11)

Next, compound (11) (1.00 g, 5.70 mmole) and toluene (100 mL) were added into a 250 mL bottle. After heating to reflux, trifluoroacetic acid (1 eq) and compound (5) (0.97 g) were added into the bottle. Next, the mixture was heated to reflux under an oxygen atmosphere. After reaction, compound (12) with a yield of 72% was obtained. The synthesis pathway was as follows:

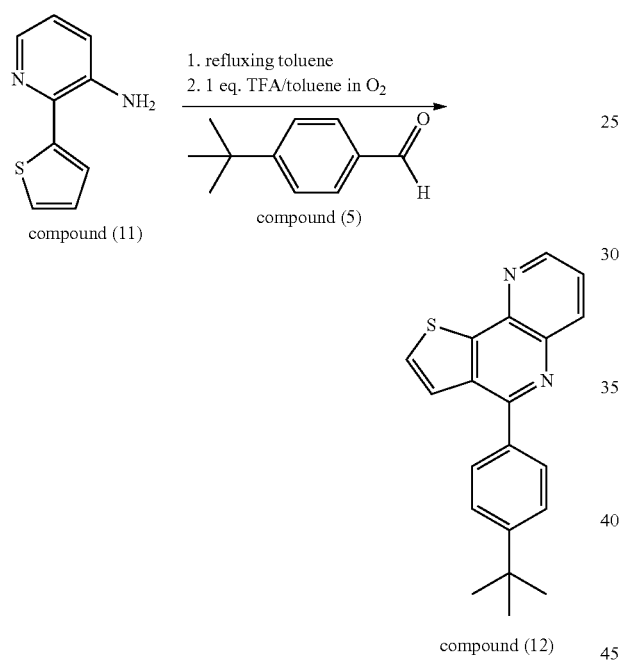

Next, compound (12) (3.68 g, 11.60 mmol), IrCl$_3$.xH2O (1.65 g), 2-methoxy ethanol (15 mL), and water (5 mL) were added into a 100 mL bottle. After heating to 140° C. for 24 hrs, acac ($\underset{\phantom{x}}{\ }$, 0.72 g), K$_2$CO$_3$ (0.76 g), and 30 mL 2-methoxyethanol were added into the bottle. After reacting for 24 hrs, the bottle was cooled down to room temperature and the reaction was quenched by adding water (50 mL). The result was purified by column chromatography with n-hexane/dichloromethane (3:1), obtaining Ir-THQ-N-acac. The synthesis pathway was as follows:

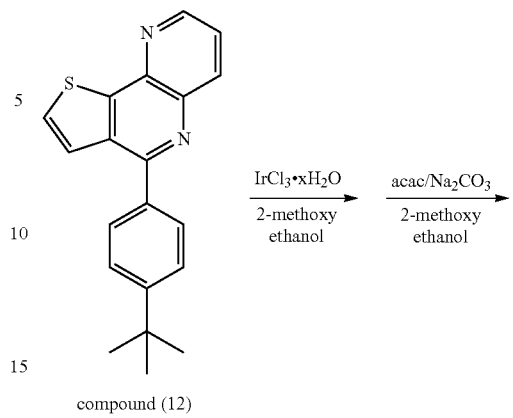

compound (12)

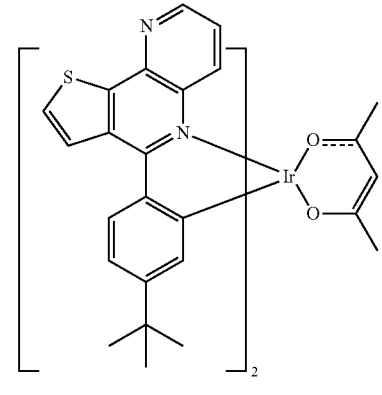

Ir-THQ-N-acac

Example 4

Preparation of Compound Ir-THQ-N-phac

Compound (12) (3.68 g, 11.60 mmol), IrCl$_3$.xH$_2$O (1.65 g), 2-methoxy ethanol (15 mL), and water (5 mL) were added into a 100 mL bottle. After heating to 140° C. for 24 hrs, compound (7) (1.30 g), K$_2$CO$_3$ (0.76 g), and 30 mL 2-methoxyethanol were added into the bottle. After reacting for 24 hrs, the bottle was cooled down to room temperature and the reaction was quenched by adding water (50 mL). The result was purified by column chromatography with n-hexane/dichloromethane (3:1), obtaining Ir-THQ-N-phac. The synthesis pathway was as follows:

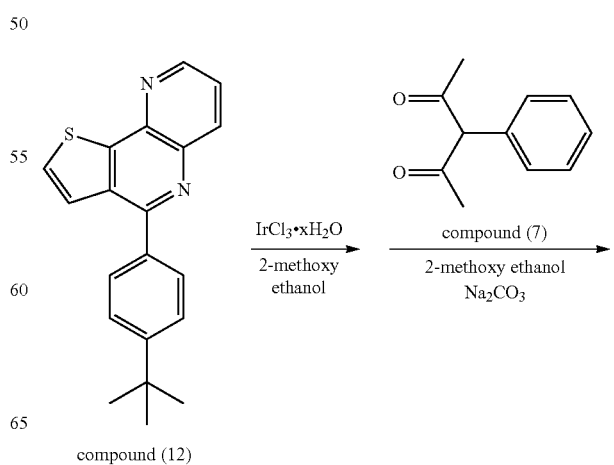

compound (12)

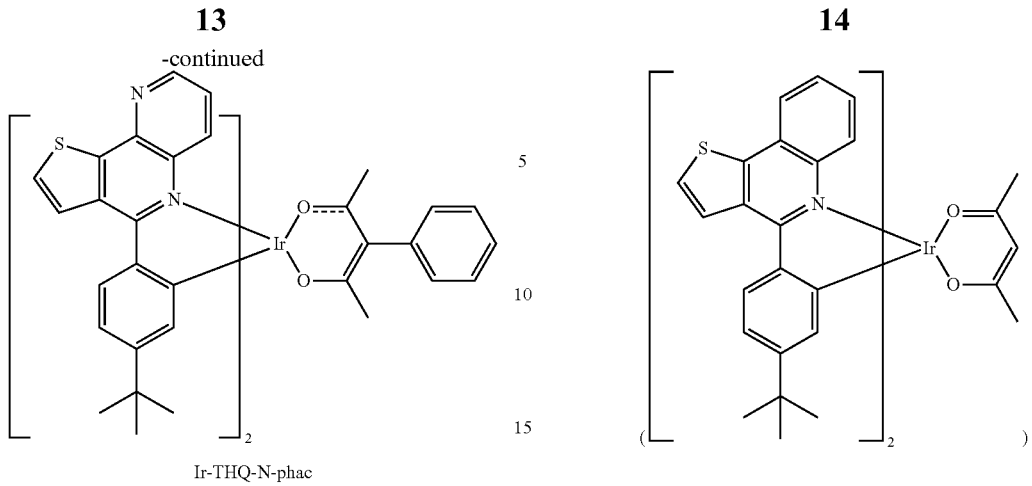

Ir-THQ-N-phac

Organic Electroluminescent Device

FIG. 1 shows an embodiment of an organic electroluminescent device 10. The electroluminescent device 100 includes a substrate 12, a bottom electrode 14, an electroluminescent element 16, and a top electrode 18, as shown in FIG. 1. The organic electroluminescent device can be top-emission, bottom-emission, or dual-emission devices.

The substrate 12 can be a glass plastic, or semiconductor substrate. Suitable materials for the bottom and top electrodes can be Ca, Ag, Mg, Al, Li, In, Au, Ni, W, Pt, Cu, indium tin oxide (ITO), indium zinc oxide (IZO), aluminum zinc oxide (AZO), or zinc oxide (ZnO), formed by sputtering, electron beam evaporation, thermal evaporation, or chemical vapor deposition. Further, at least one of the bottom and top electrodes 14 and 18 is transparent.

The electroluminescent element 16 at least includes an emission layer, and can further include a hole injection layer, a hole transport layer, an electron transport layer, and an electron injection layer. In an embodiment of the disclosure, at least one layer of the electroluminescent element 16 includes the aforementioned organometallic compound.

According to an embodiment of the disclosure, the organic electroluminescent device can be a phosphorescent organic electroluminescent device, and the phosphorescent organic electroluminescent device can include an emission layer including a host material and a phosphorescent dopant, wherein the host material includes the aforementioned organometallic compounds.

In order to clearly disclose the organic electroluminescent devices of the disclosure, the following examples (employing the organometallic compounds of Example 1 serving as dopant) are intended to illustrate the disclosure more fully without limiting their scope, since numerous modifications and variations will be apparent to those skilled in this art.

Example 5

A glass substrate with an indium tin oxide (ITO) film of 100 nm was provided and then washed with a cleaning agent, acetone, and isopropanol with ultrasonic agitation. After drying with a nitrogen flow, the ITO film was subjected to a UV/ozone treatment. Next, NPB (N,N'-di(naphthalene-1-yl)-N,N'-diphenyl-benzidine, with a thickness of 40 nm), CBP (4,4'-N,N'-dicarbazole-biphenyl) doped with Ir-THQ-acac (the ratio between CBP and Ir-THQ-acac was 100:3, with a thickness of 30 nm), Bphen (4,7-diphenyl-1,10-phenanthroline, with a thickness of 30 nm), LiF (with a thickness of 0.5 nm), and Al (with a thickness of 120 nm) were subsequently formed on the ITO film at $10^{-6}$ Pa, obtaining the electroluminescent device (1). The materials and layers formed therefrom are described in the following:

NPB (40 nm)/CBP: Ir-THQ-acac (3%) (30 nm)/Bphen (30 nm)/LiF (0.5 nm)/Al (120 nm)

The optical property of the electroluminescent device (1), as described in Example 5, was measured by a PR650 (purchased from Photo Research Inc.) and a Minolta TS110. The results are shown below:

Optimal efficiency: 34.1 cd/A, 19.5 lm/W;
Emissive efficiency: 11.9 cd/A, 4.2 lm/W@1000 cd/m²;
Electroluminescent wavelength: 612 nm;
CIE coordinations: (0.63, 0.35).

Example 6

A glass substrate with an indium tin oxide (ITO) film of 100 nm was provided and then washed with a cleaning agent, acetone, and isopropanol with ultrasonic agitation. After drying with a nitrogen flow, the ITO film was subjected to a UV/ozone treatment. Next, NPB (N,N'-di(naphthalene-1-yl)-N,N'-diphenyl-benzidine, with a thickness of 40 nm), CBP (4,4'-N,N'-dicarbazole-biphenyl) doped with Ir-THQ-acac

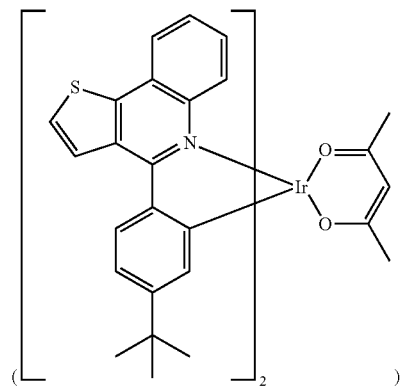

(the ratio between CBP and Ir-THQ-acac was 100:4, with a thickness of 30 nm), Bphen (4,7-diphenyl-1,10-phenanthroline, with a thickness of 30 nm), LiF (with a thickness of 0.5 nm), and Al (with a thickness of 120 nm) were subsequently formed on the ITO film at $10^{-6}$ Pa, obtaining the electroluminescent device (2). The materials and layers formed therefrom are described in the following:

NPB (40 nm)/CBP: Ir-THQ-acac (4%) (30 nm)/Bphen (30 nm)/LiF (0.5 nm)/Al (120 nm)

The optical property of the electroluminescent device (2), as described in Example 6, was measured by a PR650 (purchased from Photo Research Inc.) and a Minolta TS110. The results are shown below:

Optimal efficiency: 35.9 cd/A, 28.2 lm/W;
Emissive efficiency: 11.4 cd/A, 5.7 lm/W @1000 cd/m$^2$;
Electroluminescent wavelength: 616 nm;
CIE coordinations: (0.65, 0.34).

Example 7

A glass substrate with an indium tin oxide (ITO) film of 100 nm was provided and then washed with a cleaning agent, acetone, and isopropanol with ultrasonic agitation. After drying with a nitrogen flow, the ITO film was subjected to a UV/ozone treatment. Next, NPB (N,N'-di(naphthalene-1-yl)-N,N'-diphenyl-benzidine, with a thickness of 40 nm), CBP (4,4'-N,N'-dicarbazole-biphenyl) doped with Ir-THQ-acac

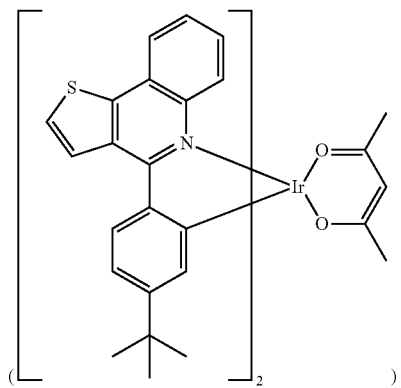

(the ratio between CBP and Ir-THQ-acac was 100:5, with a thickness of 30 nm), Bphen (4,7-diphenyl-1,10-phenanthroline, with a thickness of 30 nm), LiF (with a thickness of 0.5 nm), and Al (with a thickness of 120 nm) were subsequently formed on the ITO film at $10^{-6}$ Pa, obtaining the electroluminescent device (3). The materials and layers formed therefrom are described in the following: NPB (40 nm)/CBP: Ir-THQ-acac (4%) (30 nm)/Bphen (30 nm)/LiF (0.5 nm)/Al (120 nm)

The optical property of the electroluminescent device (3), as described in Example 7, was measured by a PR650 (purchased from Photo Research Inc.) and a Minolta TS110. The results are shown below:

Optimal efficiency: 18.7 cd/A, 9.7 lm/W;
Emissive efficiency: 10.0 cd/A, 3.5 lm/W @1000 cd/m$^2$;
Electroluminescent wavelength: 616 nm;
CIE coordinations: (0.65, 0.34).

While the disclosure has been described by way of example and in terms of the preferred embodiments, it is to be understood that the disclosure is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

Example 8

A glass substrate with an indium tin oxide (ITO) film of 100 nm was provided and then washed with a cleaning agent, acetone, and isopropanol with ultrasonic agitation. After drying with a nitrogen flow, the ITO film was subjected to a UV/ozone treatment. Next, NPB (N,N'-di(naphthalene-1-yl)-N,N'-diphenyl-benzidine, with a thickness of 40 nm), CBP (4,4'-N,N'-dicarbazole-biphenyl) doped with Ir-THQ-acac (the ratio between CBP and Ir-THQ-acac was 100:4, with a thickness of 30 nm), Bphen (4,7-diphenyl-1,10-phenanthroline, with a thickness of 30 nm), LiF (with a thickness of 0.5 nm), and Al (with a thickness of 120 nm) were subsequently formed on the ITO film at $10^{-6}$ Pa, obtaining the electroluminescent device (4). The materials and layers formed therefrom are described in the following: NPB (40 nm)/BAlq: Ir-THQ-acac (4%) (30 nm)/Bphen (30 nm)/LiF (0.5 nm)/Al (120 nm)

The optical property of the electroluminescent device (4), as described in Example 8, was measured by a PR650 (purchased from Photo Research Inc.) and a Minolta TS110. The results are shown below:

Optimal efficiency: 14.2 cd/A, 7.4 lm/W;
Emissive efficiency: 11.5 cd/A, 4.8 lm/W @1000 cd/m$^2$;
Electroluminescent wavelength: 620 nm;
CIE coordinations: (0.65, 0.35).

While the disclosure has been described by way of example and in terms of the preferred embodiments, it is to be understood that the disclosure is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An organometallic compound having a Formula (III), Formula (IV), or Formula (V), of:

Formula (III)

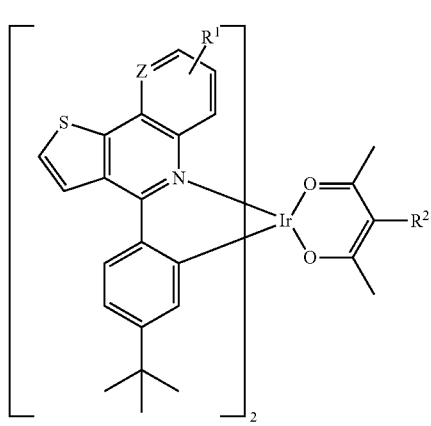

Formula (IV)

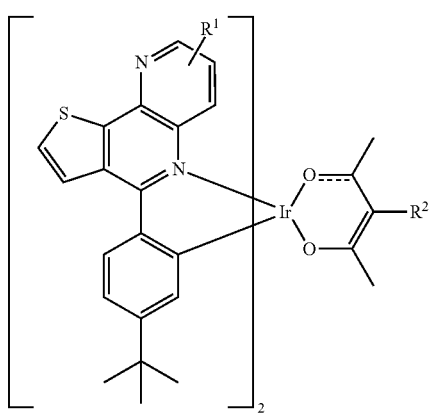

Formula (V)

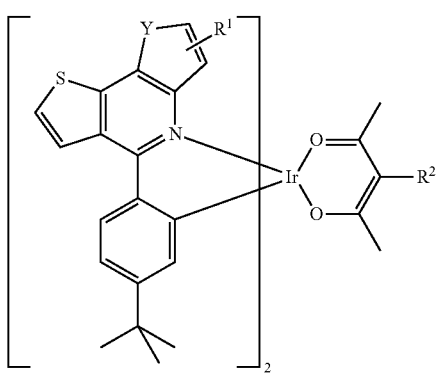

wherein, $R^1$ is hydrogen, or $C_{1-8}$ alkyl; $R^2$ is hydrogen, phenyl, or biphenyl; Z is CH; and Y is $CH_2$ or NH.

2. The organometallic compound as claimed in claim 1, wherein R1 is a methyl group, ethyl group, propyl group, isopropyl group, butyl group, tert-butyl group, pentyl group, or hexyl group.

3. The organometallic compound as claimed in claim 1, wherein the organometallic compound is

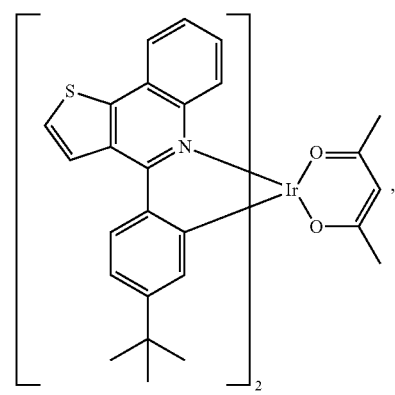

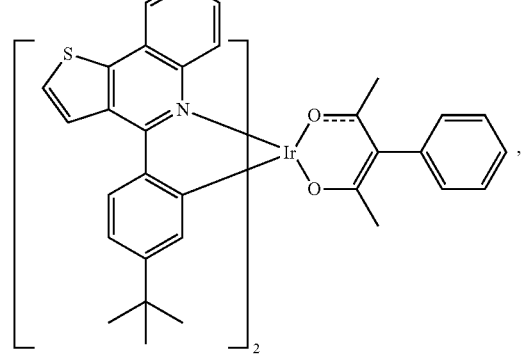

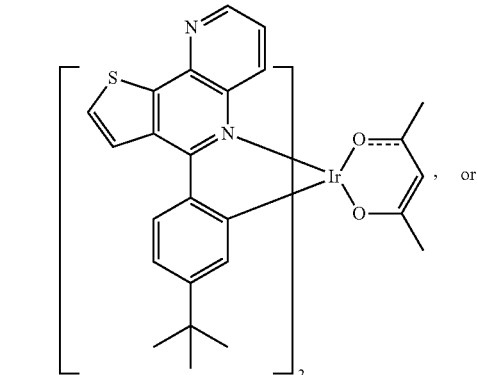

or

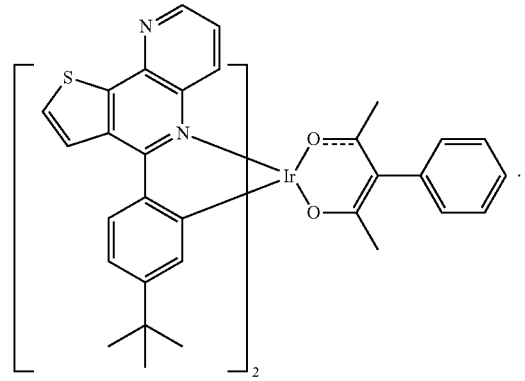

4. An organic electroluminescence device, comprising:
a pair of electrodes; and
an electroluminescent element disposed between the pair of electrodes, wherein the electroluminescent element comprises the organometallic compound as claimed in claim 1.

5. The organic electroluminescence device as claimed in claim 4, wherein the electroluminescent element emits red light under a bias voltage.

* * * * *